(12) United States Patent
Lopez-Arce et al.

(10) Patent No.: US 12,098,833 B1
(45) Date of Patent: Sep. 24, 2024

(54) POGO PIN SLOT FOR RAPID UV LIGHT MODULE REPLACEMENT

(71) Applicant: Prostar Technologies Inc., Orlando, FL (US)

(72) Inventors: Rafael Lopez-Arce, Orlando, FL (US); Brenton Bailey, Maitland, FL (US)

(73) Assignee: Prostar Technologies Inc., Orlando, FL (US)

( * ) Notice: Subject to any disclaimer, the term of this patent is extended or adjusted under 35 U.S.C. 154(b) by 0 days.

(21) Appl. No.: 18/532,824

(22) Filed: Dec. 7, 2023

(51) Int. Cl.
| | | |
|---|---|---|
| F21V 23/06 | (2006.01) | |
| A61L 9/20 | (2006.01) | |
| F21S 8/02 | (2006.01) | |
| F21V 15/02 | (2006.01) | |
| F21V 23/00 | (2015.01) | |

(52) U.S. Cl.
CPC ............ *F21V 23/06* (2013.01); *A61L 9/20* (2013.01); *F21S 8/026* (2013.01); *F21V 15/02* (2013.01); *F21V 23/006* (2013.01); *A61L 2209/111* (2013.01); *A61L 2209/12* (2013.01)

(58) Field of Classification Search
CPC ........ F21V 23/06; F21V 15/02; F21V 23/006; A61L 9/20; F21S 8/026
See application file for complete search history.

(56) References Cited

U.S. PATENT DOCUMENTS

| | | | |
|---|---|---|---|
| 5,541,826 A | 7/1996 | Sandell et al. | |
| 5,855,487 A * | 1/1999 | Kunishi | H01R 33/08 439/232 |
| 7,175,300 B1 | 2/2007 | Medeiros | |
| 10,180,245 B1 * | 1/2019 | Tang | F21K 9/233 |
| 2008/0061809 A1 | 3/2008 | Lee et al. | |
| 2019/0221978 A1 * | 7/2019 | Harte | H01R 13/4532 |
| 2019/0234593 A1 * | 8/2019 | Stevens | F21V 23/023 |
| 2021/0010662 A1 * | 1/2021 | Dixit | F21S 8/04 |
| 2021/0116107 A1 | 4/2021 | Li et al. | |
| 2021/0313733 A1 * | 10/2021 | Martin | H01R 13/70 |
| 2022/0090771 A1 | 3/2022 | May | |
| 2022/0249718 A1 | 8/2022 | Rifkin | |
| 2022/0260525 A1 | 8/2022 | Molho et al. | |

FOREIGN PATENT DOCUMENTS

| | | |
|---|---|---|
| CN | 108626636 | 10/2018 |
| CN | 215259441 | 12/2021 |
| CN | 218333802 | 1/2023 |
| TW | M373434 | 2/2010 |

\* cited by examiner

*Primary Examiner* — Christopher E Dunay
(74) *Attorney, Agent, or Firm* — Vierra Magen Marcus LLP

(57) ABSTRACT

A UV sanitization system includes a UV lamp fixture for housing an ultraviolet (UV) lamp module. A slot of the UV lamp fixture includes a pair of depressible pogo pins configured to make contact with electrodes of the UV lamp module. The slot of the UV lamp fixture further includes a ramp configured to guide the UV lamp module into the slot to a position where the UV lamp electrodes snap into engagement with pogo pins to provide haptic feedback to the user that the lamp module is fully and properly inserted into the slot. The UV lamp module may be just as easily removed, simply by gripping edges of the UV lamp module and removing it from the slot.

20 Claims, 15 Drawing Sheets

POGO PIN SLOT FOR RAPID UV LIGHT MODULE REPLACEMENT

FIELD

The present technology generally relates to ultraviolet (UV) sanitization.

BACKGROUND

Ultraviolet electromagnetic radiation (light) has been introduced as a means to sanitize. Ultraviolet (UV) light has been classified into at least four bands depending upon the effects upon the skin of humans and other animals. Such bands include UV-A, which is defined as ultraviolet light having a wavelength in a range from 315 nm to 400 nm; UV-B, which is defined as ultraviolet light having a wavelength in a range from 280 nm to 315 nm; UV-C, which is defined as ultraviolet light having a wavelength that is in a range from 235 nm to 280 nm; and Far UV, which is defined as ultraviolet light having a wavelength that is in a range from 185 nm to 235 nm.

Ultraviolet light in the UV-C range has been used for sanitization. For example, UV light emitted at 254 nm and 265 nm has been used to destroy viruses and other microorganisms for a number of years. Far UV light (e.g., 222 nm) has been shown to have efficacy for this use as well.

The safety of UV light to humans is dependent on the wavelength and light intensity. UV light in the UV-C range can have harmful impacts on humans. For example, prolonged direct exposure to UV-C light can result in eye and skin damage, such as acute corneal injury (sometimes referred to as "welder's eye") and acute erythema. Acute effects from UV-C light include redness, ulceration or burns of the skin. However, far-UVC is unable to penetrate the tear layer of the eyes or the dead skin layer.

There are different types of UV lamps, including for example excimer (excited dimer) lamps, mercury vapor lamps and halide lamps. Different types of lamps have different lifespans, but eventually, all UV lamps require replacement. At present, the process for replacing UV lamps is complicated and time consuming, typically requiring a specialized technician for each such UV lamp replacement. Currently, UV lamps are mounted within a lamp housing that is in turn mounted within a UV lamp fixture by a number of structural components, screws, and hardwired electrical connections. Thus, in order to replace a UV lamp, the technician must be called to the site, the technician must then partially or completely disassemble the lamp fixture, insert the new UV lamp, and the reassemble the lamp fixture. Considering that a facility may employ hundreds or more UV lamps for sanitizing the facility, it becomes a considerable burden to keep all such lamps in working order.

BRIEF DESCRIPTION OF THE DRAWINGS

Aspects of the present disclosure are illustrated by way of example and are not limited by the accompanying figures for which like references indicate elements.

DETAILED DESCRIPTION

Figure 1:
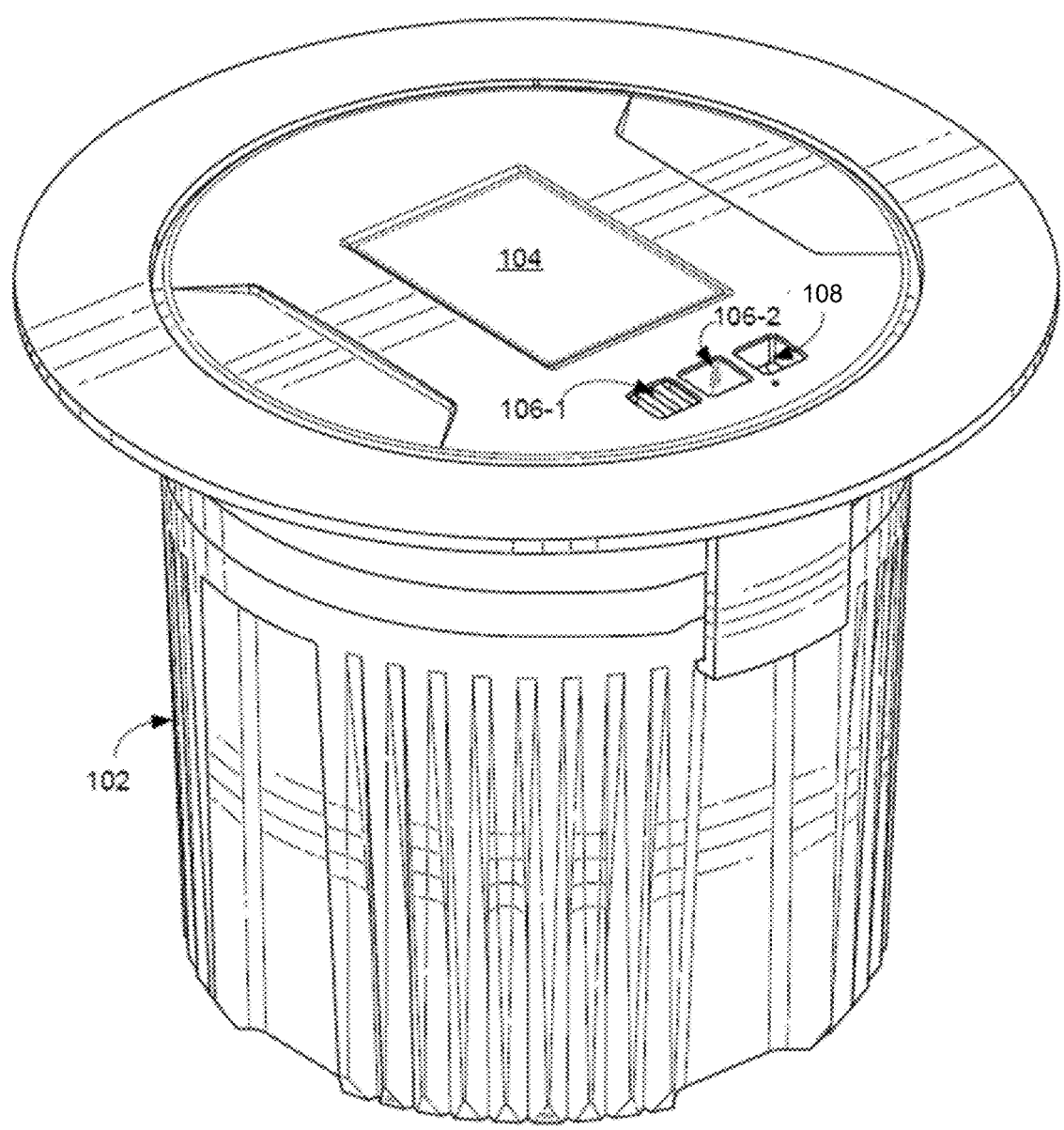
FIG. 1 illustrates a perspective view of a UV sanitization system according to embodiments of the present technology.

The present disclosure will now be described with reference to the figures, which in general relate to UV sanitization. An embodiment includes a UV sanitization system including a UV lamp fixture for housing an ultraviolet (UV) lamp module. The UV lamp module is configured to emit UV light into an environment in which the UV sanitization system is present to sanitize the area around the UV lamp module. In accordance with aspects of the present technology, the UV lamp module may be quickly and easily inserted into and removed from a slot of the UV lamp fixture.

The slot of the UV lamp fixture includes a pair of depressible pogo pins configured to make contact with electrodes of the UV lamp module. The slot of the UV lamp fixture further includes a ramp configured to guide the UV lamp module into the slot to a position where the UV lamp electrodes snap into engagement with pogo pins to provide haptic feedback to the user that the lamp module is fully and properly inserted into the slot. The UV lamp module may be just as easily removed, simply by gripping edges of the UV lamp module and removing it from the slot.

UV lamp assemblies produce significant amounts of electromagnetic radiation. In accordance with further aspects of the present technology, in order to protect the electronics of the UV sanitation system against electromagnetic interference (EMI) from the UV lamp module radiation, the UV lamp fixture may further include a number of metal plates positioned in the fixture to form a Faraday cage around the UV lamp module.

It is understood that the present embodiments of the disclosure may be implemented in many different forms and that claims scopes should not be construed as being limited to the embodiments set forth herein. Rather, these embodiments are provided so that this disclosure will be thorough and complete and will fully convey the inventive embodiment concepts to those skilled in the art. Indeed, the disclosure is intended to cover alternatives, modifications and equivalents of these embodiments, which are included within the scope and spirit of the disclosure as defined by the appended claims. Furthermore, in the following detailed description of the present embodiments of the disclosure, numerous specific details are set forth in order to provide a thorough understanding. However, it will be clear to those of ordinary skill in the art that the present embodiments of the disclosure may be practiced without such specific details.

The terms "top" and "bottom," "upper" and "lower" and "vertical" and "horizontal," and forms thereof, as may be used herein are by way of example and illustrative purposes only, and are not meant to limit the description of the technology inasmuch as the referenced item can be exchanged in position and orientation. Also, as used herein, the terms "substantially" and/or "about" mean that the specified dimension or parameter may be varied within an acceptable manufacturing tolerance for a given application. In one embodiment, the acceptable manufacturing tolerance is ±0.25 mm, or alternatively, ±2.5% of a given dimension.

For purposes of this disclosure, a physical or electrical connection may be a direct connection or an indirect connection (e.g., via one or more other parts). In some cases, when a first element is referred to as being connected, affixed, mounted or coupled to a second element (either physically or electrically), the first and second elements may be directly connected, affixed, mounted or coupled to each other or indirectly connected, affixed, mounted or coupled to each other (either physically or electrically). When a first element is referred to as being directly connected, affixed, mounted or coupled to a second element, then there are no intervening elements between the first and second elements (other than possibly an adhesive or melted metal used to connect, affix, mount or couple the first and second elements).

FIG. 1 illustrates one embodiment of a UV sanitization system 100 in accordance with the present technology. The UV sanitization system 100 has a housing 102 that contains various electronic circuits. The housing 102 includes a UV lamp module 104 which may be used for sanitation. One example of UV lamp module 104 is an excimer UV lamp that emits UV light in a wavelength that is in a range from 185 nm to 235 nm. It is understood that other UV lamp assemblies may be used. The housing 102 holds the UV lamp module 104 in a position to allow the lamp 104 to emit UV light into an environment in which the UV sanitization system 100 resides. One or more sensors 106-1, 106-2 and an LED 108 are present near the UV lamp module 104. The sensors 106-1, 106-2 and LED 108 are explained in greater detail below, but in general, the one or more sensors 106-1, 106-2 are used to sense environmental conditions within the environment in which the UV sanitization system 100 resides.

Figure 2:
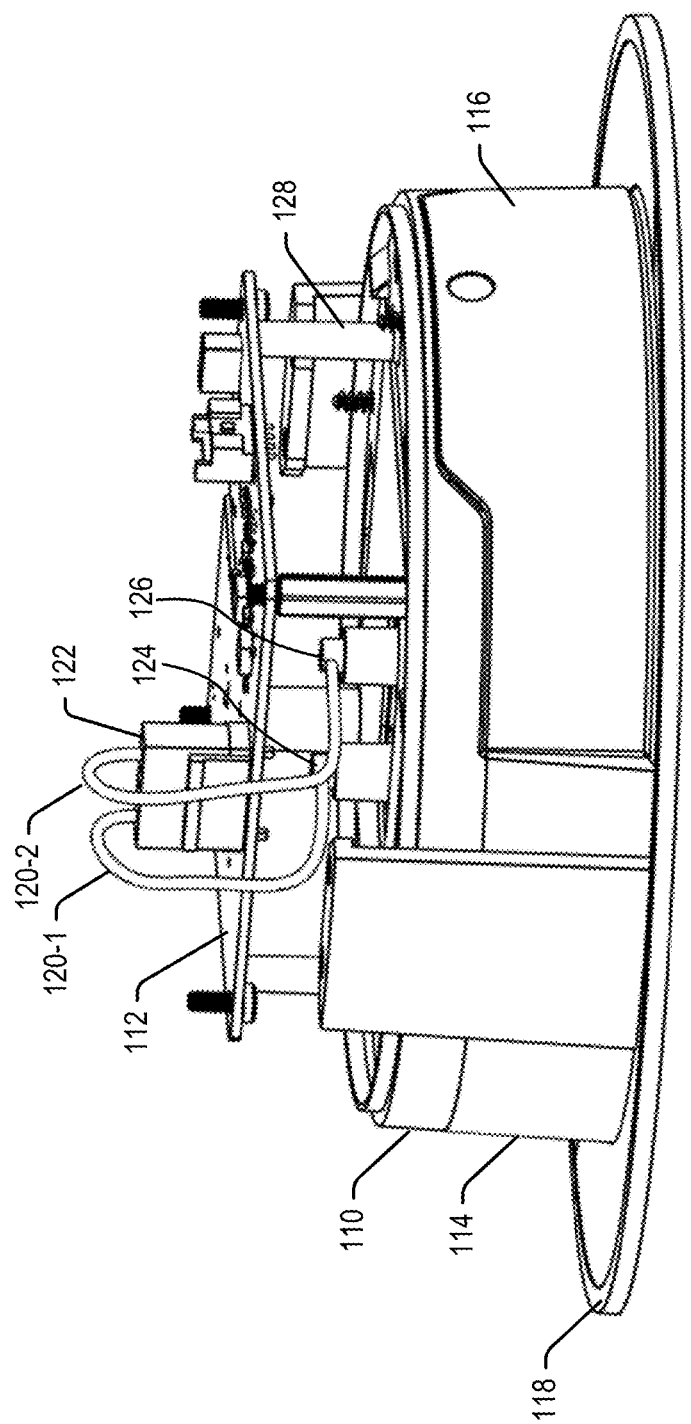
FIG. 2 is a perspective view of a lamp fixture of the UV sanitization system according to embodiments of the present technology.

FIG. 2 is a perspective view showing a portion of the sanitization system 100. In particular, FIG. 2 shows a UV lamp fixture 110 that houses the UV lamp module 104, and an inverter circuit board 112 to power and control the operation of the UV lamp module 104. The UV lamp fixture 110 incudes a housing 114 having a removable cover plate 116 which covers a slot for receiving the UV lamp module 104 as explained below. In embodiments, the housing 114 may be formed of ⅛ inch to ¼ inch polycarbonate to prevent the heat generated by the UV lamp module from affecting the inverter board 112 or other components. It is understood that the housing 114 may be formed of other materials and other thicknesses in further embodiments. The lamp fixture 110 further includes a ceiling plate 118 for mating the lamp fixture within a ceiling canister in the ceiling where the sanitization system 100 is mounted.

The inverter circuit board 112 receives power from the facility of the sanitization system 100 and converts it to voltage and frequency required by the UV lamp module 104. A typical UV lamp module 104 will require a high voltage and current to initiate and maintain UV light production. The inverter circuit board 112 provides power to the UV lamp module 104 via high/low voltage leads 120-1, 120-2, which connect to the inverter circuit board 112 via a wire harness connector 122 that plugs into the inverter circuit board 112. In accordance with aspects of the present technology, the high/low voltage leads 120-1, 120-2 connect to the UV lamp fixture 110 and UV lamp module 104 via a pair of high/low voltage pogo pins 124, 126, the structure and operation of which are explained below.

The inverter circuit board 112 may be affixed to and spaced from the UV lamp fixture 110 via posts 128 (one of which is numbered in FIG. 2). The posts 128 are sized to space the inverter circuit board 112 away from the UV fixture 110 and UV lamp module 104 to minimize cross talk and EMI effects on the board 112 from UV lamp radiation. In one example, the posts 128 may be 1 inch long, but they may be longer or shorter in further embodiments.

Figure 3:
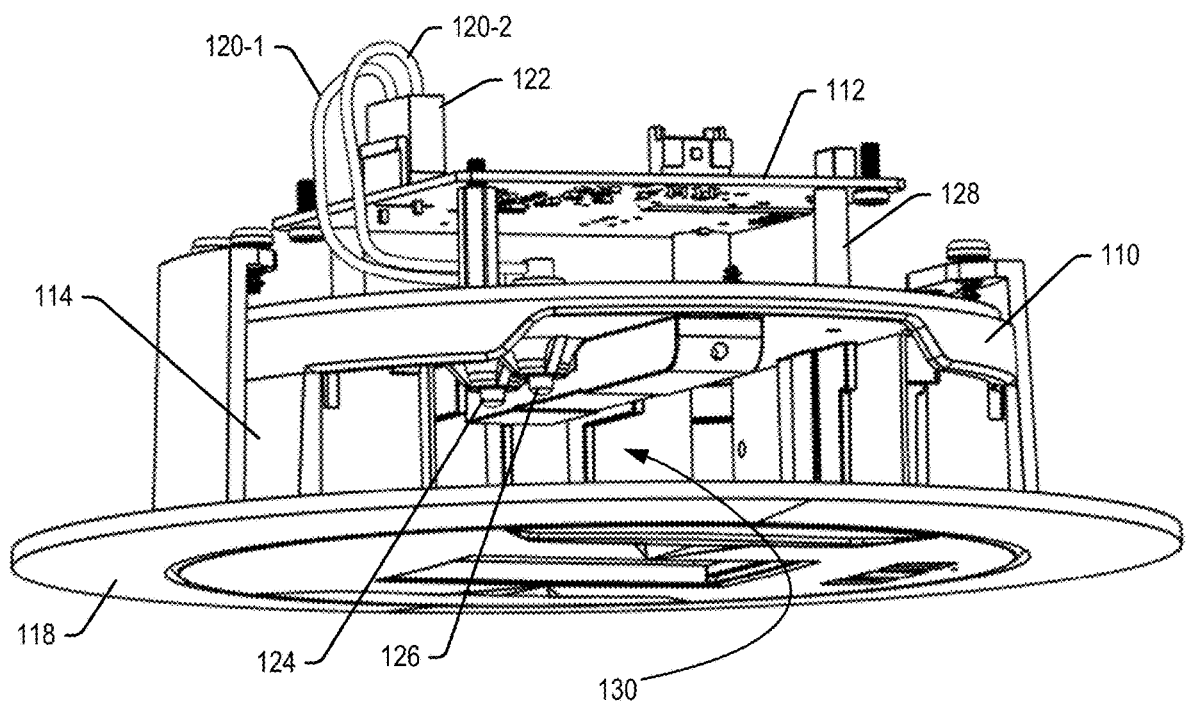
FIG. 3 is a perspective view of a lamp fixture of the UV sanitization system with a slot cover removed according to embodiments of the present technology.
Figure 4:
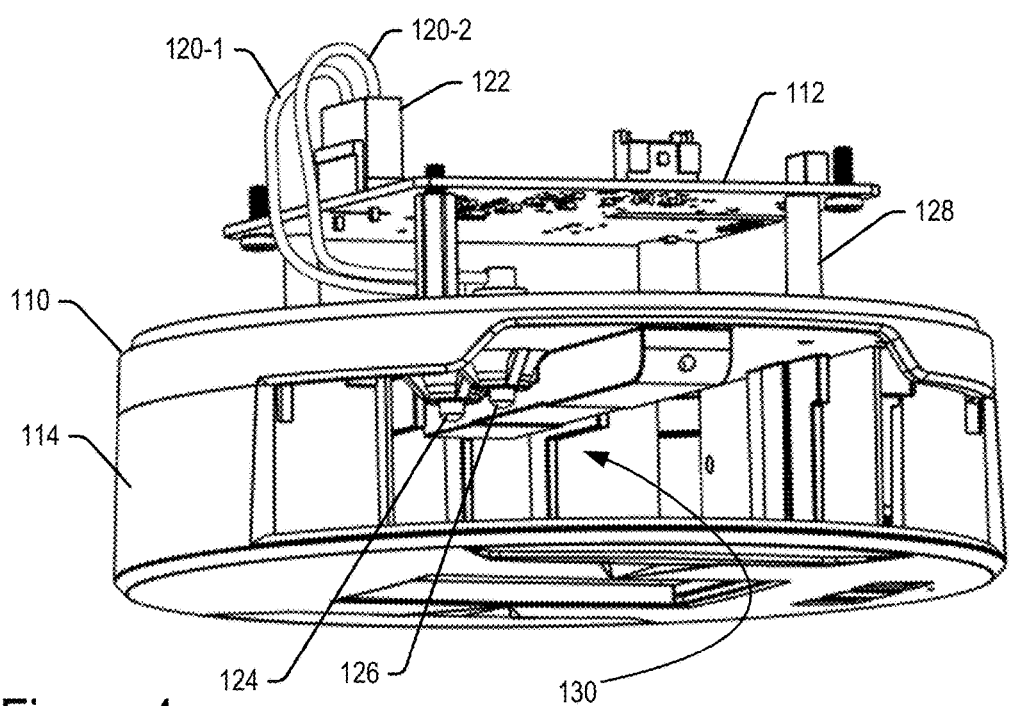
FIG. 4 is a perspective view of a lamp fixture of the UV sanitization system with a slot cover and ceiling plate removed according to embodiments of the present technology.
Figure 5:
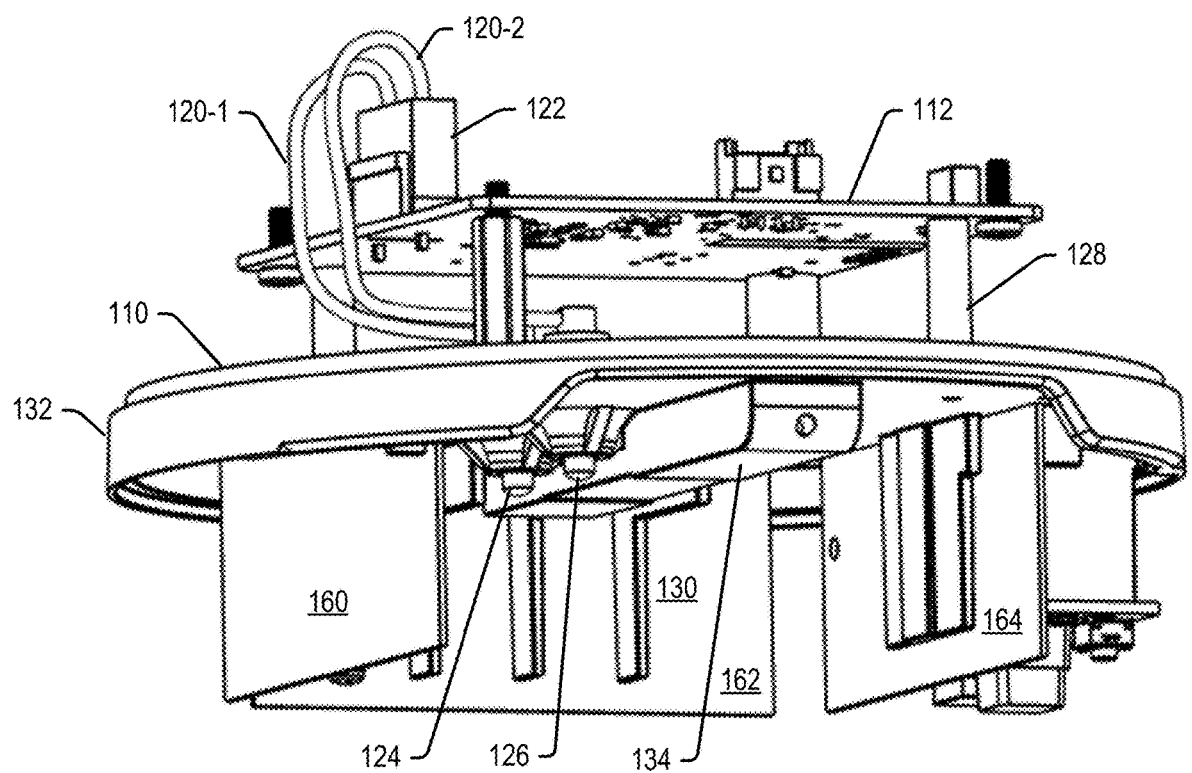
FIG. 5 is a perspective view of a lamp fixture of the UV sanitization system with a slot cover, ceiling plate and lamp fixture cover removed according to embodiments of the present technology.
Figure 6:
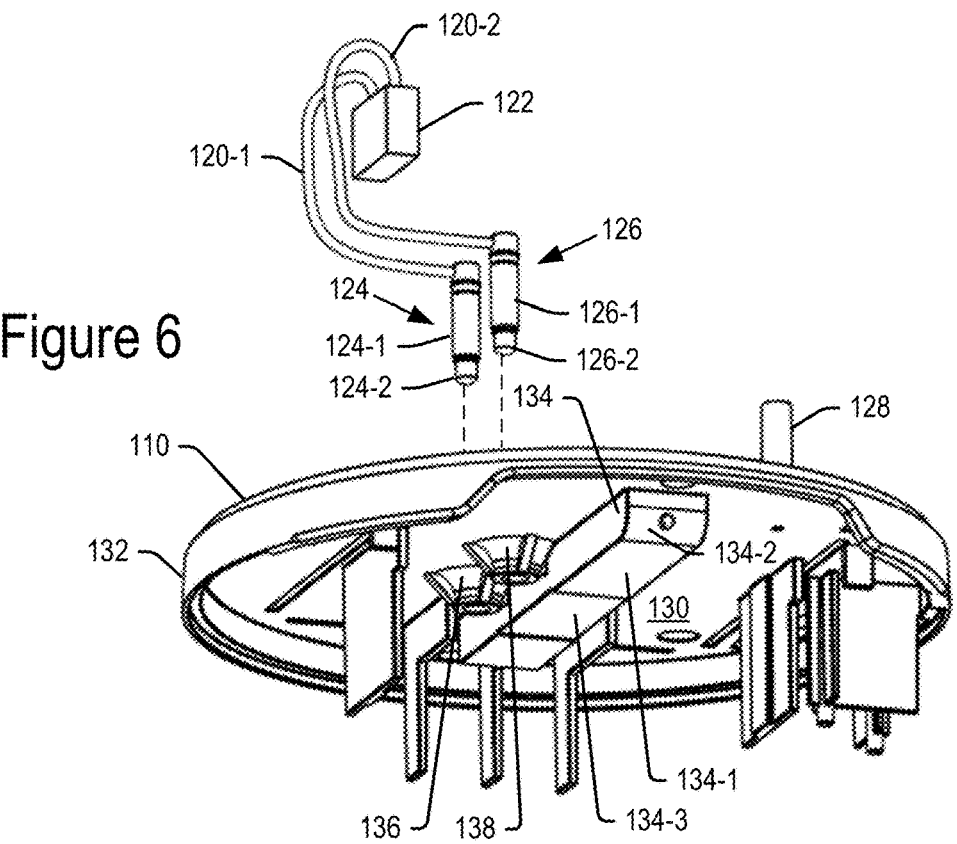
FIG. 6 is an exploded perspective view of a lamp fixture baseplate and pogo pins according to embodiments of the present technology.
Figure 7:
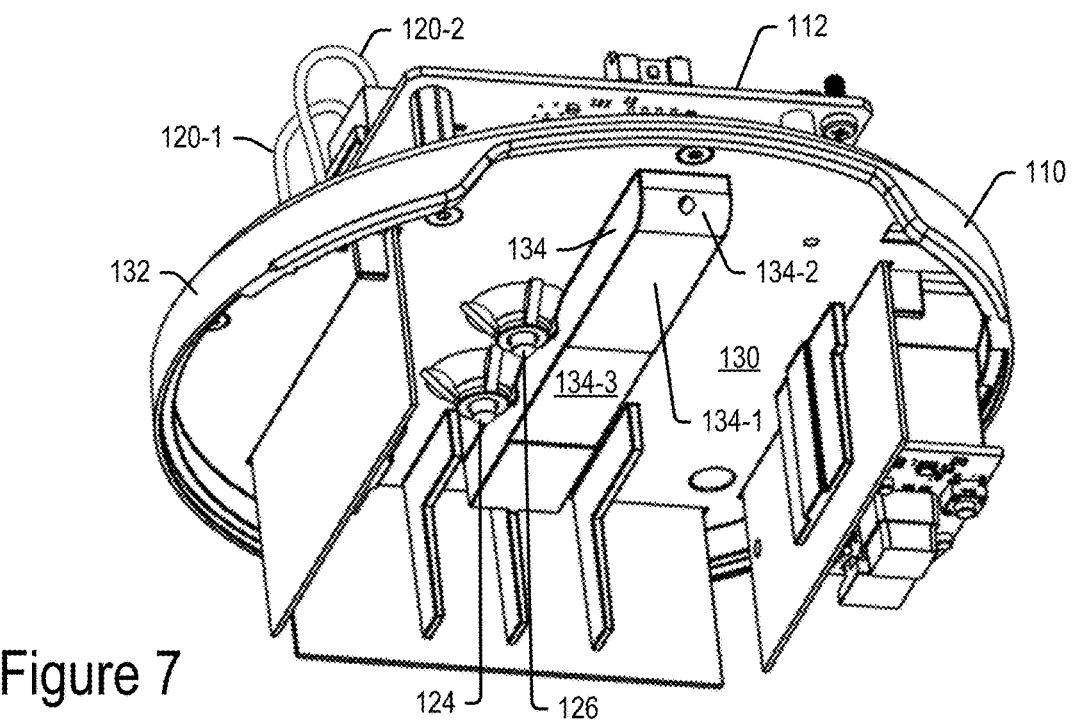
FIG. 7 is a perspective view of a lamp fixture baseplate, Faraday cage and inverter board according to embodiments of the present technology.

FIGS. 3 and 4 are perspective views of the UV light fixture 110 and inverter circuit board 112 similar to FIG. 2, but in FIG. 3, the removable cover plate 116 omitted, and in FIG. 4, the ceiling plate 118 is further omitted. FIGS. 5-7 are additional perspective views of the UV light fixture 110 and inverter circuit board 112 similar to FIG. 4, but with the housing 114 further removed. FIGS. 3 and 4 show an interior of a slot 130 defined within the housing 114 for receiving the UV lamp module 104. FIGS. 5-7 show further detail of the components within the interior slot 130.

As shown in these figures, slot 130 is defined by a base plate 132 on which is formed a ramp 134 for guiding the UV lamp module 104 into the slot 130, and for guiding electrodes of the UV lamp module into contact with the high/low voltage pogo pins 124 and 126. The UV lamp module 104 is not shown in FIGS. 3-7. The ramp 134 is formed on the base plate 132 with a longitudinal axis along its length, and to have a surface 134-1 at an elevation spaced from the base plate 132 that is parallel along its length to a surface of the base plate 132. Ramp 134 includes a rounded or sloped lead-in section 134-2 to facilitate insertion of the lamp module 104. Ramp 134 further includes a recessed section 134-3 at a second elevation spaced from the base plate so as to be recessed into surface 134-1. The recessed section 134-3 facilitates engagement of the electrodes of the UV lamp module 104 with the high/low voltage pogo pins 124, 126 as explained below. The recessed section 134-3 may be parallel to the distal surface 134-1.

The ramp 134 may have a front to back length of between 4 and 5 inches, a depth from base plate 132 of 0.4 to 0.5 inches, and a width of 0.5 to 0.7 inches. Each of these dimensions may vary, proportionately or disproportionately to each other, in further embodiments. The recessed section 134-3 may be recessed 1 mm into the surface 134-1, and may have a length of ¾ inches and a width equal to the width of ramp 134. The ramp 134, as well as other features on the base plate 132, may be integrally formed with each other, for example by additive manufacturing or casting.

FIG. 6 is an exploded perspective view showing the baseplate 132 and the high/low voltage pogo pins 124, 126. The pogo pins 124, 126 may be mounted to the base plate 132 within a pair of fixtures 136, 138 integrally formed with and extending from the base plate 132. FIGS. 5 and 7, for example, show the pogo pins 124, 126 mounted within the fixtures 136, 138. The fixtures 136, 138 are positioned adjacent the ramp 134, where the amount of adjacency is dictated by positions of the electrodes in the UV lamp module 104 as explained below. The fixtures 136, 138 may be aligned with each other along a line parallel to a length of the ramp 134.

Referring to FIG. 6, the pogo pins 124, 126 each include cylindrical base sections 124-1, 126-1 which are fixedly mounted within fixtures 136 and 138. First ends of the base sections 124-1, 126-1 extend out of the fixtures 136, 138 at a backside of the base plate 132 to receive the leads 120-1 and 120-2 to supply the high and low voltages from the inverter board 112 to the pogo pins 124, 126. Second ends of the base sections 124-1, 126-1 include cylindrical plungers 124-2, 126-2 mounted for translation within the base sections 124-1, 124-2. Each pogo pin 124, 126 further includes an internal spring (not shown) within base sections 124-1, 126-1 which biases the plungers 124-2, 126-2 into their extended positions.

As explained below, upon insertion of the UV lamp module 104 into slot 130, electrodes on the UV lamp module contacts the pogo pins 124, 126, overcoming the force of the internal springs and depressing the plungers 124-2, 126-2 into base sections 124-1, 126-1. This contact provides the operational voltage to the UV lamp module 104. The pogo pins 124, 126 are engineered to strict parameters: i) for enhanced electrical performance, ii) to enable the proper, easy, repeatable and reliable insertion of the UV lamp module 104 and iii) to enable the proper, repeatable and reliable contact of the electrodes of the UV lamp module 104 with the pogo pins 124, 126.

Regarding the electrical characteristics of the pogo pins 124, 126, the pins are required to transfer high voltage and high currents necessary for proper performance of the UV lamp module 104. In one example, the UV lamp module 104 uses 4 kV to 6 kV and 11 Watts of power. To meet these demanding electrical requirements, the pogo pins 124, 126 are formed of brass. Additionally, a gold plating treatment may be performed to gold-plate the pogo pins 124, 126 to further enhance their electrical conductivity, resulting in low electrical resistivity. This composition of the pogo pins guarantees a reliable and stable electrical connection, minimizing any potential disruptions to the UV lamp's operation.

Moreover, the springs within the pogo pins 124, 126 are calibrated to exert a spring force controlling depression of the plungers 124-2, 126-2 that produces continuous contact with the electrodes of the UV lamp module 104 upon full insertion of UV lamp module 104. In one example, the plungers are configured to depress 3 mm when acted on by the UV lamp module electrodes. At this depression, the spring force may be 700 gf. This design feature ensures a secure and stable connection between the pogo pins and UV lamp electrodes. The spring force also allows the UV lamp module 104 to be inserted and removed without applying excessive force, reducing the risk of damaging the module 104 or the fixture 110. Moreover, the calibrated springs provide the pogo pins 124, 126 with a haptic response when the module 104 is fully inserted. This tactile feedback gives users a clear indication when the UV lamp module 104 is fully and properly inserted.

Furthermore, the geometry and amount of depression of the plungers 124-2, 126-2 are highly controlled to enable proper insertion of the UV lamp module, including passage of the first lamp electrode over the front pogo pin 138 enroute to its engagement with the rear pogo pin 136. This interaction of the UV lamp module electrodes with the pogo pins is explained in greater detail below. However, in one example, the plungers 124-2, 126-2 may have a diameter of 3.9 mm, and each may depress 3 mm when acted on by the UV lamp module electrodes. The plungers 124-2, 126-2 may have a rounded distal tip having a radius of 2.5 mm. It is conceivable that one or more of these dimensions may vary in further embodiments, depending on the type of electrodes used in the UV lamp module.

Figure 8A:
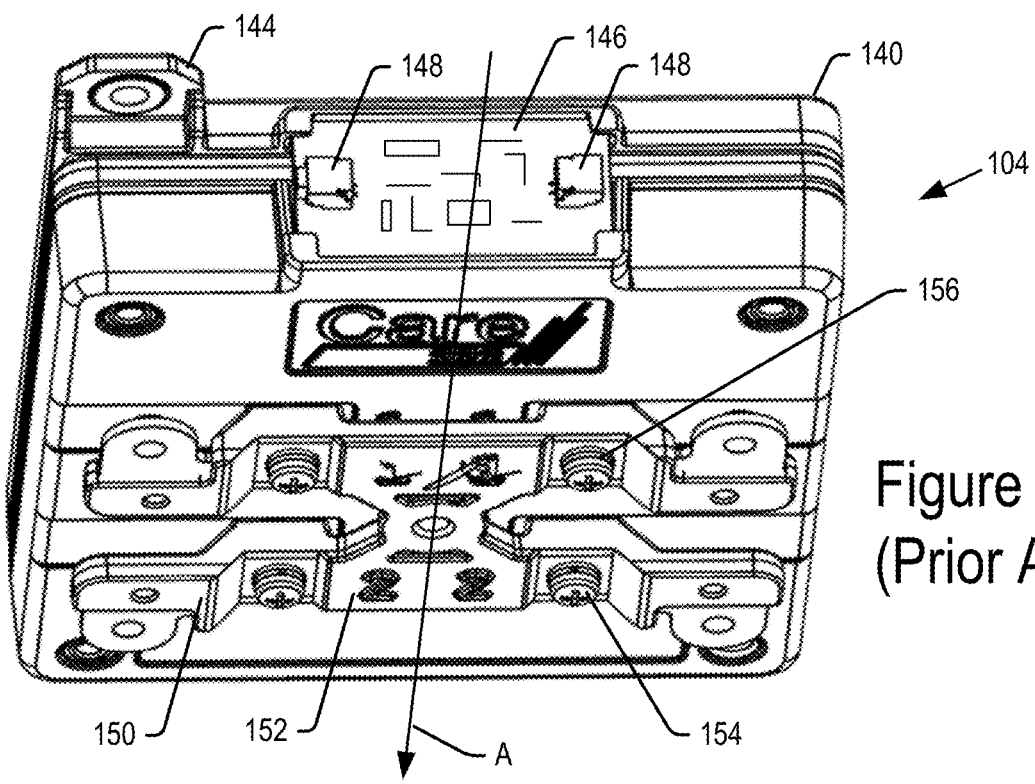
FIGS. 8A and 8B are perspective views of a conventional UV lamp module including an electrode bracket according to embodiments of the present technology.
Figure 8B:
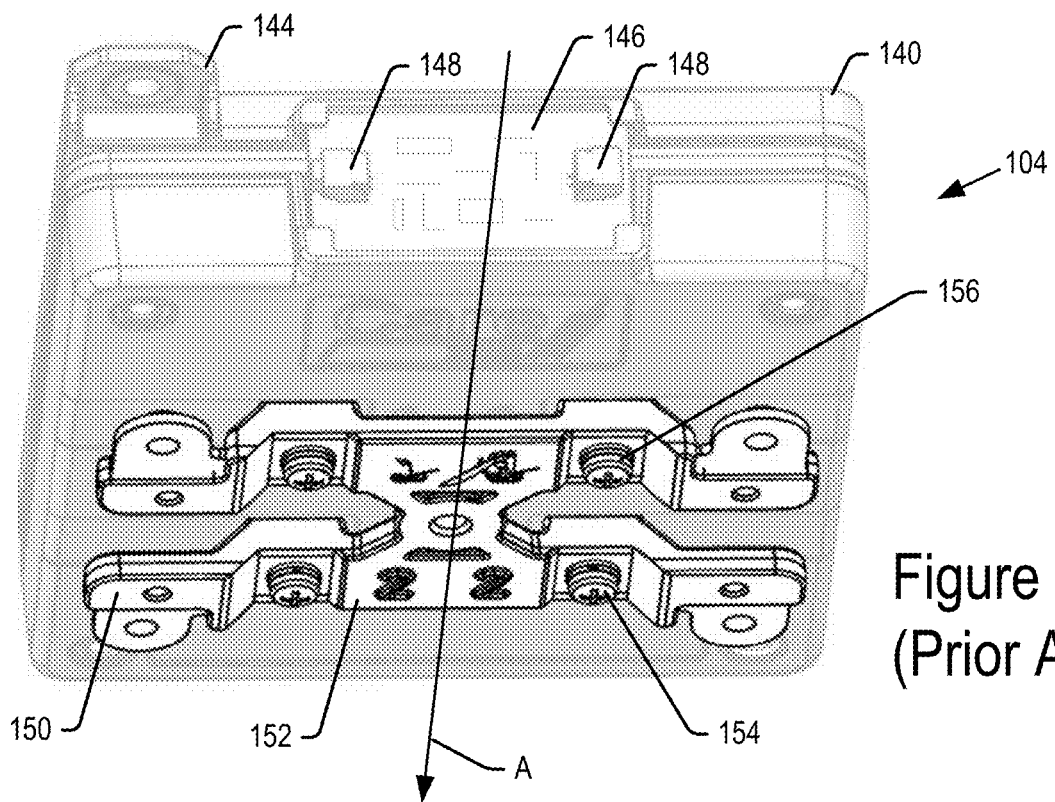

FIGS. 8A and 8B are perspective views of an example of a conventional, off-the-shelf UV lamp module 104 that may be used in the UV lamp fixture 110 according to the present technology. In an embodiment, the UV lamp fixture 110 is configured to operate with a Care222® excimer-type UV lamp module manufactured by Ushio America, Inc. having a place of business in California, US. However, it is conceivable that the UV lamp fixture 110 be customized to operate with different types of UV lamp assemblies. In general, the UV lamp module 104 includes a lamp housing 140 enclosing a UV lamp 142 (seen for example in FIG. 9). The housing 140 includes screw fastening holes 144 (and other features) which are used to affix the lamp module in conventional fixtures, but which are unnecessary in the fixture 110 of the present technology. A circuit board 146 is mounted in the housing 140 which serves a number of functions, including regulating the power supplied by pogo pins 124, 126, for controlling operation of the UV lamp 142, for example to manage on/off cycles, and for providing communication functions for monitoring and diagnostics. The circuit board further includes socket connectors 148 for receiving a pin connector coupling signal wires from the inverter circuit board 112 to the UV lamp module 104 upon insertion of the UV lamp module as explained below.

The UV lamp module 104 further includes an electrode bracket 150 including a central slide plate 152, and two pairs of electrodes 154, 156. Only one of these pairs of electrodes 154, 156 is used to electrically couple the UV lamp module 104 to the fixture 110. As shown, the electrodes 154, 156 may be in the form of screws which, in addition to transferring power from the fixture 110 to the UV lamp module 104, serve to affix the electrode bracket 150 to the housing 140. FIG. 8B is identical to FIG. 8A, but in FIG. 8B, the lamp housing is shown in phantom so that the entirety of the electrode bracket 150 may be more easily discerned.

Figure 9:
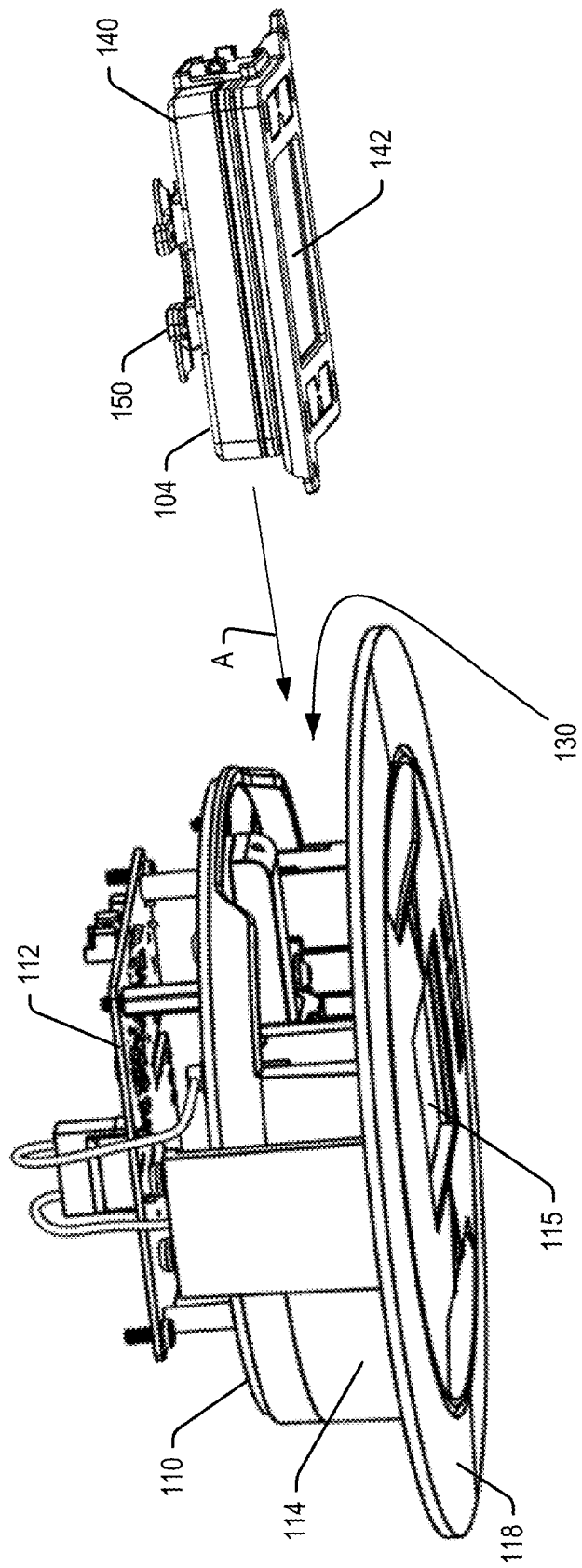
FIG. 9 is a perspective view of a conventional UV lamp module positioned for insertion into the slot of a UV lamp fixture according to embodiments of the present technology.

Insertion of the UV lamp module 104 into the slot 130 in fixture 110 will now be described in greater detail with reference to FIGS. 8A-15. Referring initially to FIG. 9, the UV lamp module 104 is manually inserted into the slot 130 along the longitudinal axis of the ramp indicated by arrow A in FIGS. 8A-9, with the UV lamp 142 facing downward and electrode bracket 150 facing upward as shown. As the UV lamp module 104 enters the slot 130, the electrode bracket 150 will engage the lead-in section 134-2 of ramp 134. The electrode bracket 150, and specifically, the slide plate 152, will thereafter slide along the ramp 134. The slot 130 is sized so that the UV lamp module 104 fits snugly in slot 130 left to right and top to bottom. This ensures that the slide plate 152 remains aligned and centered on the ramp 134 as the module 104 is inserted into the slot.

Figure 10:
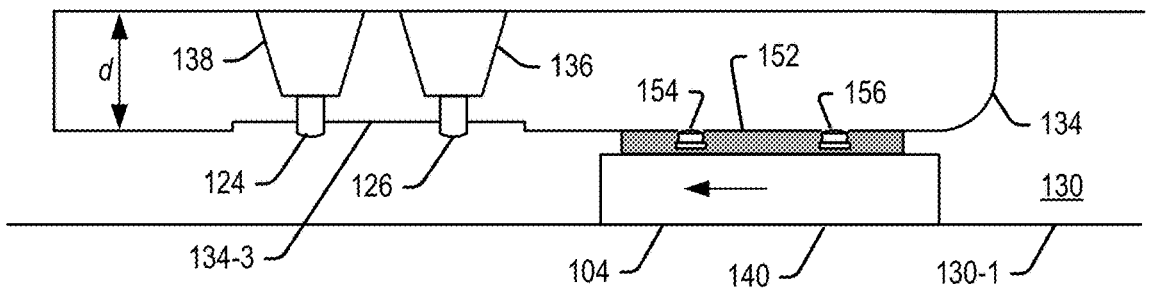
FIGS. 10-12 are cross-sectional edge views showing the interaction of the UV lamp fixture ramp and the electrode bracket of the UV lamp module according to embodiments of the present technology.
Figure 11:
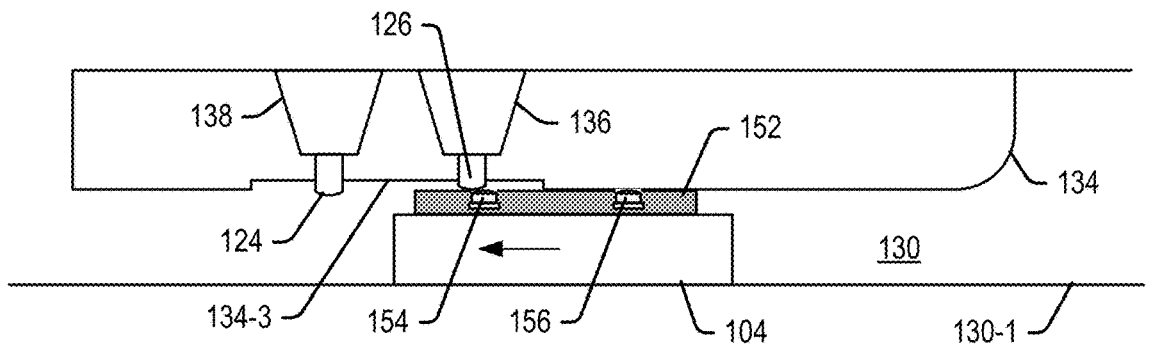
Figure 12:
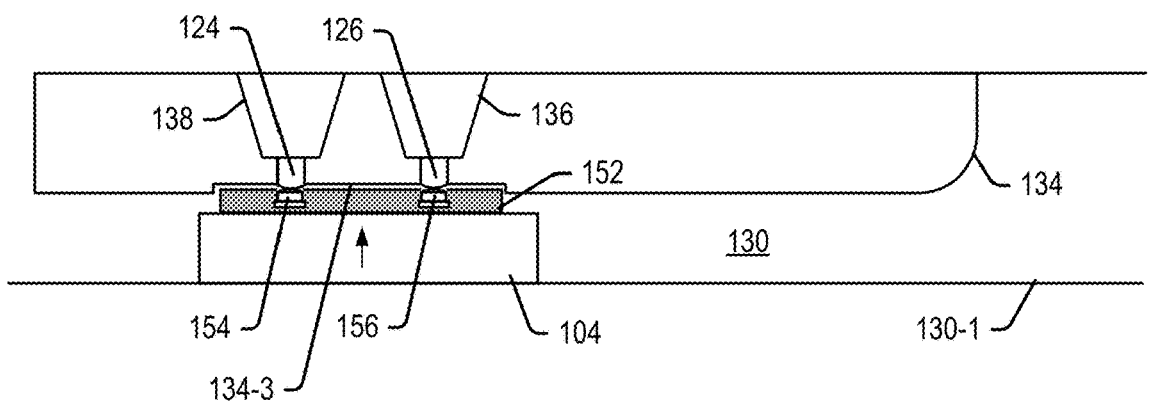

FIGS. 10-12 are cross-sectional edge views of the UV lamp module 104 as it is manually inserted into slot 130. FIG. 10 shows the initial engagement of the slide plate 152 with ramp 134. As noted above, the ramp 134 is provided with a depth, d (except at recess 134-3, where the depth is smaller). The depth, d, is provided so that there is a snug, pressure fit between the slide plate 152 and ramp 134 on one side of the UV lamp module 104, and between a top surface of the lamp housing 140 and a bottom surface 130-1 of the slot 130 on the opposed side of the UV lamp module 104. The lamp module 104 is manually pushed rearward into the slot 130, with the slide plate 152 riding along ramp 134 and the lamp electrodes 154, 156 riding along next to the ramp 134.

Referring now to FIG. 11, at some point during the rearward insertion of the UV lamp module 104 the leading electrode 154 will encounter pogo pin 126, which is nearer to the entrance to slot 130 than pogo pin 124. At this point, the leading electrode 154 temporarily depresses pogo pin 126 into fixture 136 as the electrode 154 moves past pogo pin 126. If the pogo pin 126 is too long, or if there is insufficient radius at the distal tip of pogo pin 126, the electrode 154 will crash into a vertical edge of the pogo pin 126 and prevent proper insertion of the UV lamp module 104. Conversely, if the pogo pins 124, 126 are too short, they will not engage the electrodes 154, 156 and the UV lamp module 104 will not receive power. As noted above, the geometry and dimensions of the pogo pins 124, 126 are provided to ensure that as the leading electrode 154 passes pogo pin 126, electrode 154 engages the radiused distal tip of the pogo pin 126 to temporarily depress pogo pin 126.

As also seen in FIG. 11, a leading edge of the slide plate 152 of the UV lamp module 104 has cleared a leading edge of the recess 134-3 of the ramp 134. However, as the trailing edge of the slide plate 152 remains engaged with the ramp 134, the UV lamp module 104 continues its translation into slot 130 without any upward movement of the module 104 into recess 134-3.

Referring now to FIG. 12, the UV lamp module 104 is manually inserted until the trailing edge of slide plate 152 clears the leading edge of the recess 134-3. At this point, given the snug, pressure fit of the UV lamp module 104 against ramp 134, the slide plate 152 snaps upward into recess 134-3. The positions and spacings of the pogo pins 124, 126 are provided relative to the recess 134-3 and electrodes 154, 156 such that, when the slide plate 152 snaps upward into recess 134-3, the electrodes 154, 156 are directly aligned with pogo pins 124, 126. The snapping of the slide plate 152 into recess 134-3 also depresses the pogo pins 124, 126 into their respective fixtures 136, 138 against the bias of the springs internal to the pogo pins. This ensures a firm, pressure contact between electrode 154 and pogo pin 124, and a firm, pressure contact between electrode 156 and pogo pin 126.

The snapping of the slide plate 152 up into recess 134-3 provides haptic feedback to the user that the lamp module 104 is fully and properly inserted into the slot 130. The contact of the electrodes 154, 156 against the pogo pins 124, 126 as well as the depression of the pogo pins 124, 126 may also or alternatively provide haptic feedback to the user that the lamp module 104 is fully and properly inserted into the slot 130.

Figure 13:
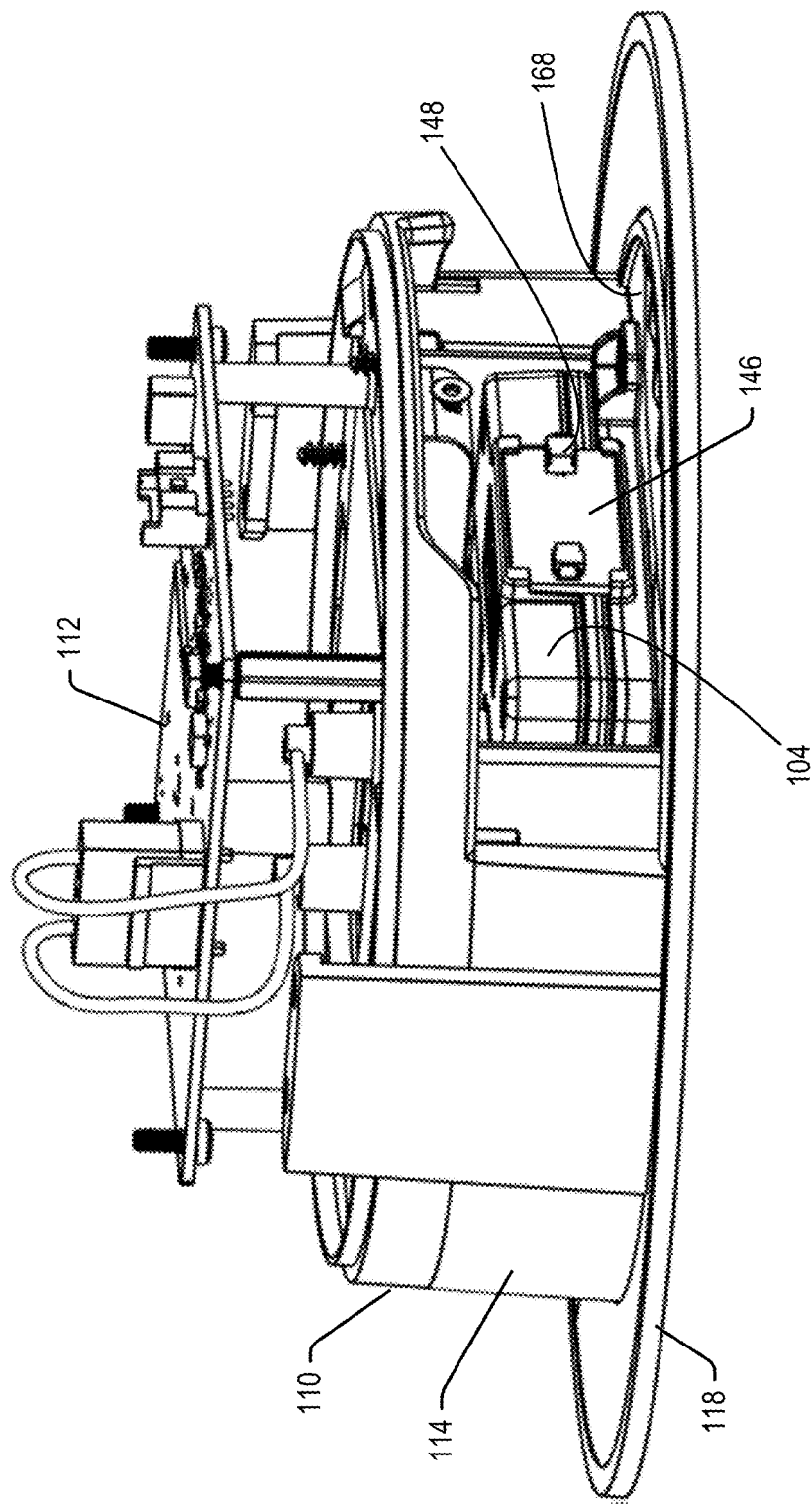
FIG. 13 is a perspective view of a conventional UV lamp module inserted into the slot of a UV lamp fixture according to embodiments of the present technology.
Figure 18:
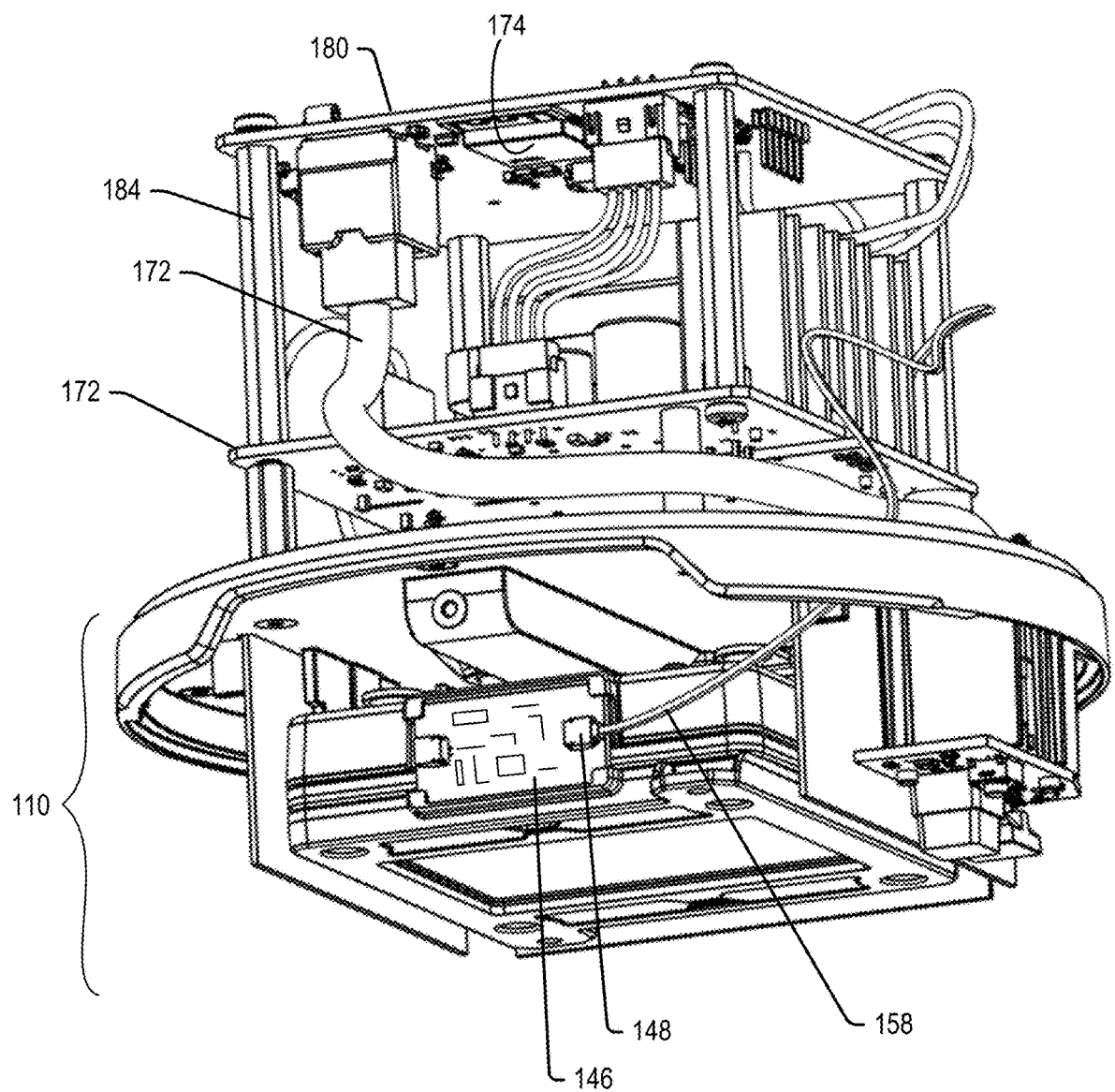
FIG. 18 is a first perspective view of the UV lamp module and the UV lamp fixture, the inverter circuit board and the sensor circuit board with cover plates removed according to embodiments of the present technology.
Figure 19:
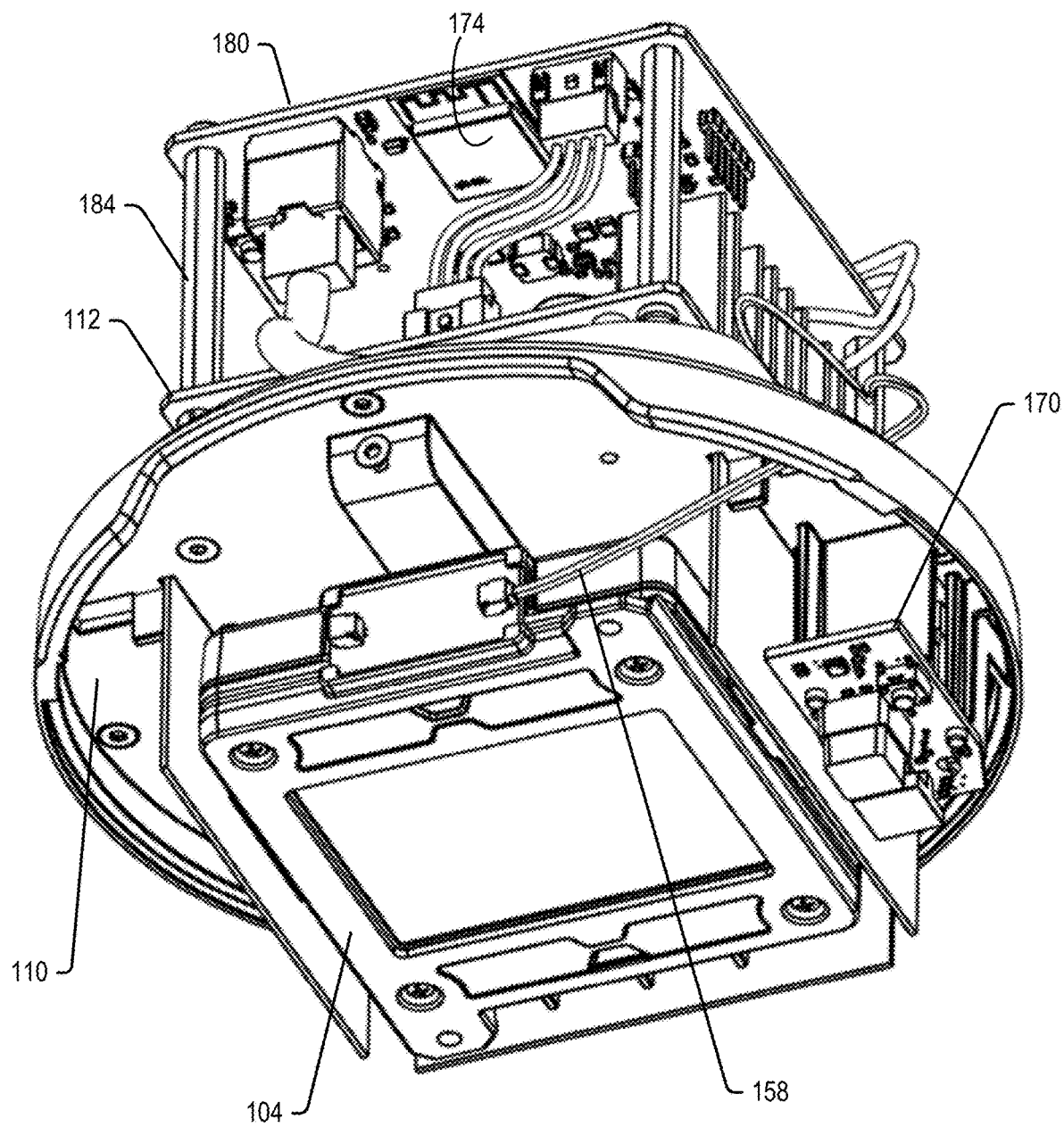
FIG. 19 is a second perspective view of the UV lamp module and the UV lamp fixture, the inverter circuit board and the sensor circuit board with cover plates removed according to embodiments of the present technology.

FIG. 13 is a perspective view showing the UV lamp module 104 fully inserted into the slot 130 of fixture 110. In this position, the UV lamp module 104 receives power from the pogo pins 124 126 as described above. Also, in this position, the UV lamp 142 within lamp module 104 is properly aligned with a window 115 (FIG. 9) in the housing 114 to emit UV light into the environment of the UV sanitization system 100. At this point, electrical pin connector 158 (FIGS. 18 and 19) from the inverter board 112 may be connected to one of the connectors 148 in circuit board 146 of the UV lamp module 104 to allow signal transfer and communication between the UV sanitization system 100 and the UV lamp module 104.

Figure 14:
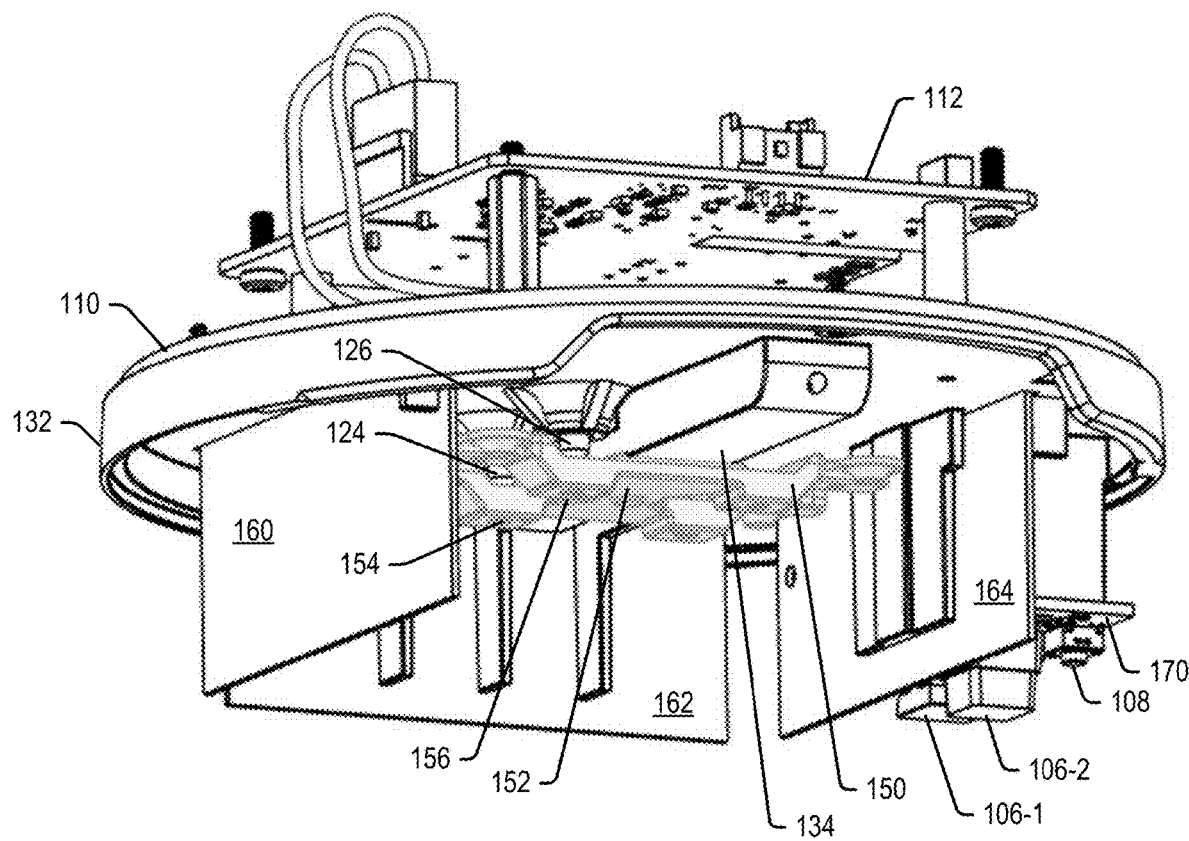
FIG. 14 is a first partial perspective view of the electrode bracket of a UV lamp module positioned against the pogo pins within the slot of a UV lamp fixture according to embodiments of the present technology.
Figure 15:
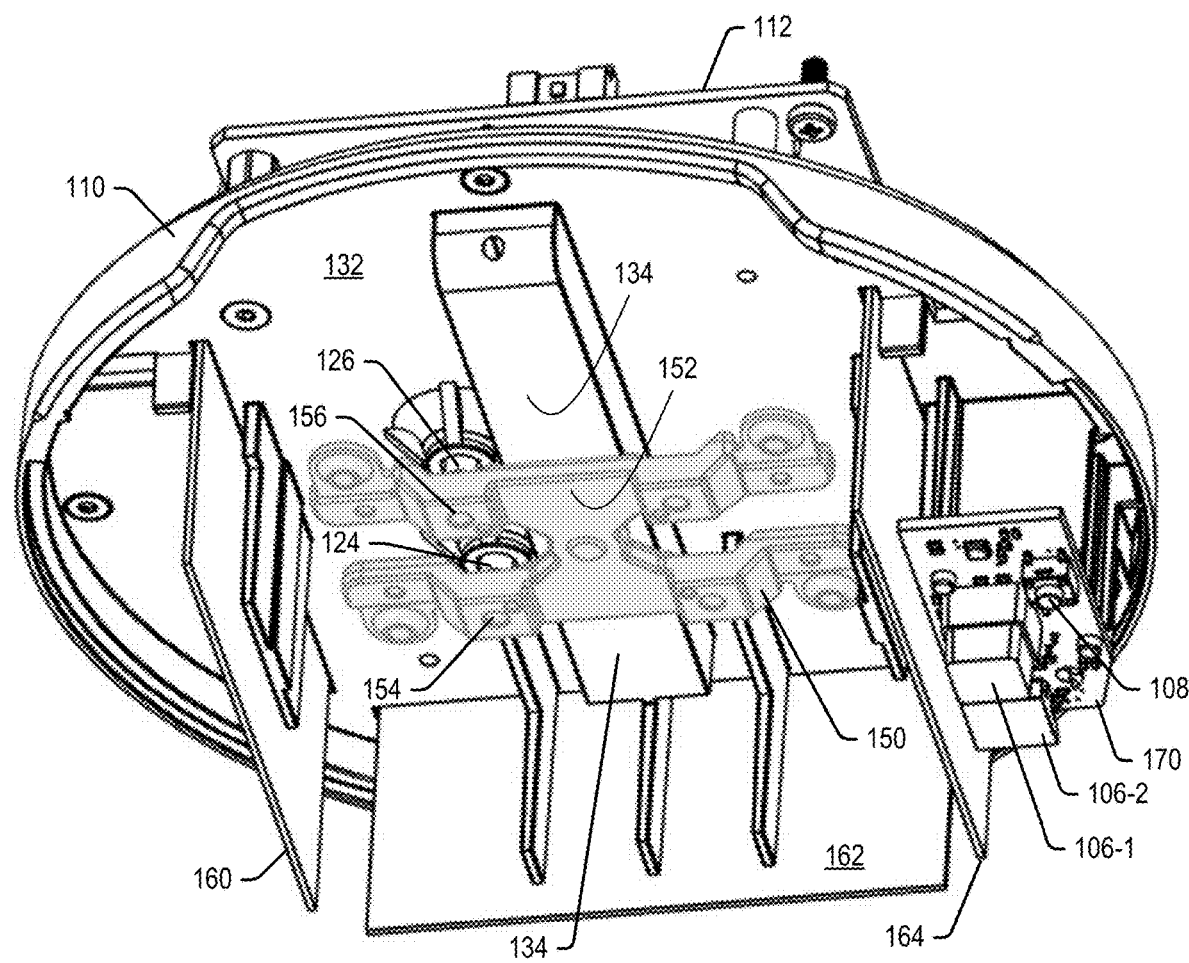
FIG. 15 is a second partial perspective view of the electrode bracket of a UV lamp module positioned against the pogo pins within the slot of a UV lamp fixture according to embodiments of the present technology.
Figure 16:
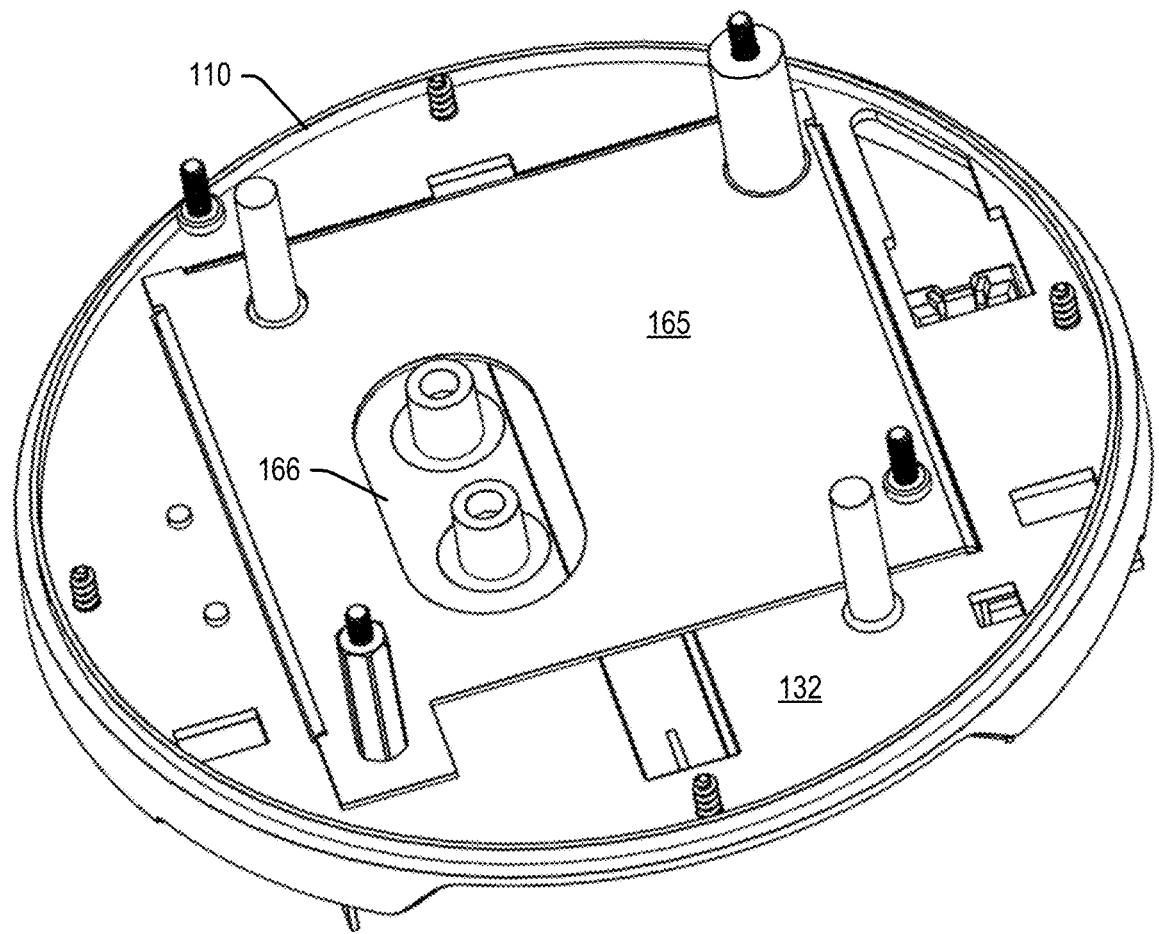
FIG. 16 is a perspective view of a back surface of the UV lamp fixture according to embodiments of the present technology.

FIGS. 14 and 15 are views from two different perspectives further illustrating the interaction of slide plate 152 with ramp 134 and interaction of the electrodes 154, 156 with pogo pins 124, 126. In the views of FIGS. 14 and 15, the housing 114 of fixture 110 is omitted. FIGS. 14 and 15 also show just the electrode plate 150, shown shaded in the figures. The housing 140 of the UV lamp module 104 is omitted for clarity. These and other figures illustrate the position and engagement of the slide plate 152 with the ramp 134, with the slide plate 152 being positioned in the recess 134-3 upon full insertion. These and other figures also show the position and engagement of the electrodes 154, 156 with the pogo pons 124, 126 upon full insertion of the UV lamp module 104, with the electrodes 154, 156 being positioned directly over the pogo pins 124, 126 and depressing the pogo pins 124, 126.

During operation, the UV lamp module 104 generates electromagnetic radiation. In order to protect the inverter board, sensor board and other electronics in the UV sanitization system 100 against EMI from this radiation, a Faraday cage may be built around the slot 130. FIGS. 14 and 15, for example, show plates 160, 162 and 164 forming three sides of the Faraday cage. These plates may be formed out of metal such as aluminum or copper, and may be mounted within slots formed in the base plate 132. A fourth metallic plate is mounted to the opposed side of the base plate. Such a plate 165 is shown in the perspective view of the opposed side of the base plate 132 in FIG. 15. The plate 165 may include a slot 166 through which extend bosses for receiving the pogo pins 124. 126.

A fifth metallic plate may be formed in the housing on the opposed side of the slot 130 from the base plate 132. A small portion of such a plate 168 is shown in FIG. 13. Although not shown, the plate 168 includes an opening surrounding the window 115 (FIG. 9) within which the UV lamp 152 is positioned upon full insertion of the UV lamp module 104. These five plates together form a Faraday cage around five sides of the UV lamp module 104. Wires (not shown) may connect these plates to ground through the ceiling canister within which the sanitization system 100 is mounted. Although not shown, it is possible that the cover plate 116 (FIG. 2) include a metallic plate on its interior surface to surround the UV lamp module with the Faraday cage on its sixth side.

As noted earlier, the sanitization system 100 according to the present technology includes various sensors 106-1, 106-2 used to sense environmental conditions within the environment in which the UV sanitization system 100 resides. These sensors are mounted on a sensing circuit board 170 as seen for example in FIGS. 14 and 15. The sensors 106-1, 106-2 may be provided for sensing various parameters of the environment surrounding the sanitization system 100, including for example some or all of air composition, temperature, barometric pressure, air quality index, relative humidity, illuminance and VOCs (Volatile Organic Compounds).

These parameters are measured by the sensors 106-1, 106-2, which in turn generate digital signals representing sensor readings. These digital signals are transmitted by an electrical connector 172 to a sensor control chip 174 (FIGS. 17 and 18), mounted on a main circuit board 180 as explained hereinafter. The sensor control chip 174 may in turn provide input to a control circuit for the UV lamp module 104 to adjust and optimize the UV light emitted by the module 104 to maximize its effectiveness at sanitizing the environment around the UV lamp module 104. While two sensors 106-1 and 106-2 are shown, there may be a single sensor or more than two sensors in further embodiments. As mentioned earlier, an LED indicator 108 may further be provided on the sensor circuit board 170 for indicating a status of the UV lamp module 104.

Figure 17:
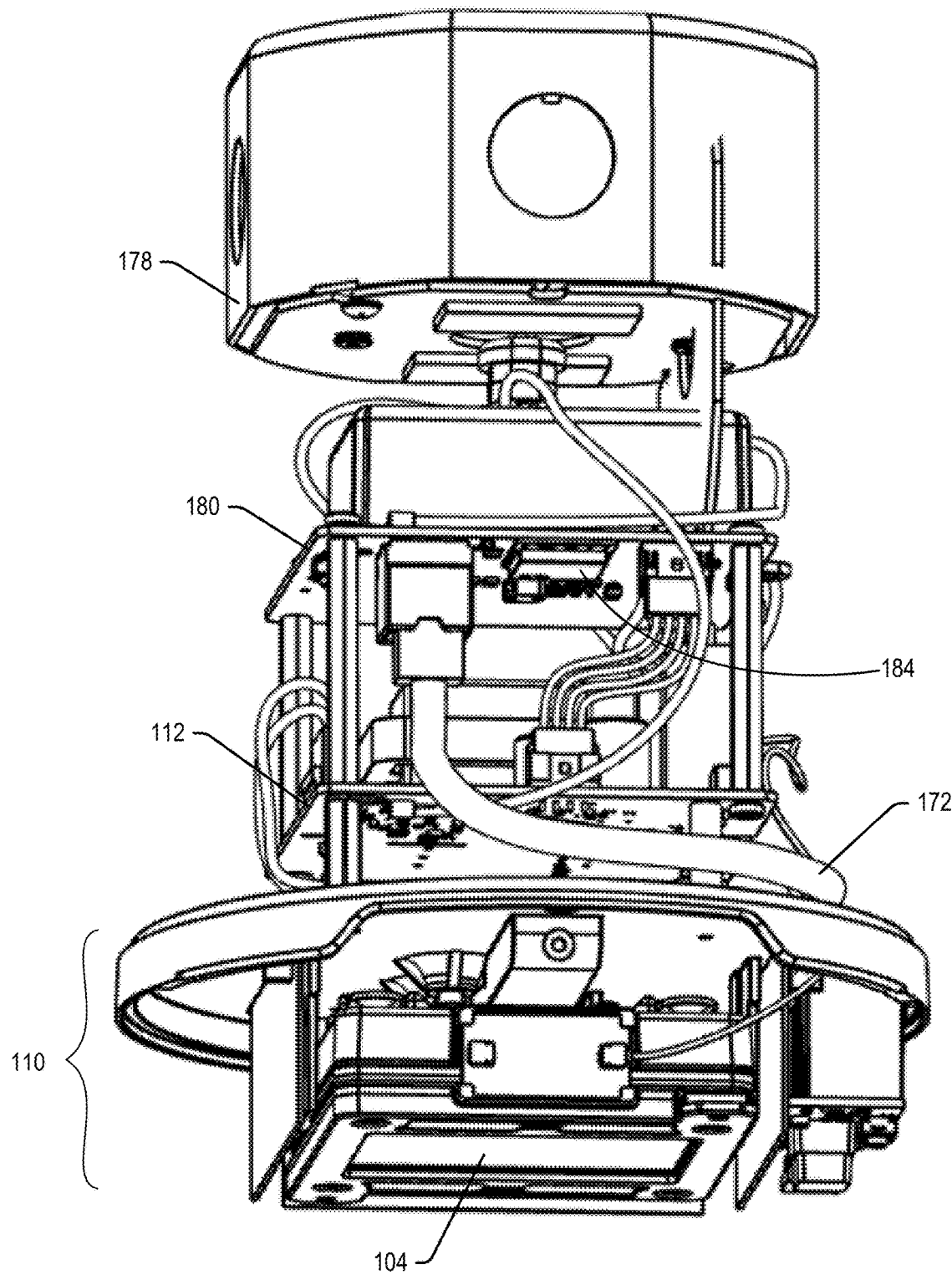
FIG. 17 is a perspective view of the UV sanitization system with cover plates removed.

FIG. 17 is a perspective view of the entire sanitization system 100, with various housings and cover plates removed to show the interior components of the sanitization system 100. The sanitization system 100 is shown mounted to a ceiling canister 178, which provides a mounting bracket for the system 100, and electrical grounding and power from the facility power supply. Interior portions of the fixture 110, described in detail above, are shown at the bottom of the air sanitization system, with a UV lamp module 104 mounted therein. The sanitization system 100 further includes three circuit boards, though there may be more or less in further embodiments. The inverter circuit board 112 and the sensor circuit board 170 have been discussed above. The sanitization system 100 further includes a main circuit board 180. Details of the three circuit boards are shown in FIG. 17 and the enlarged partial views of FIGS. 18 and 19.

The main circuit board 180 contains a control circuit for controlling the overall operation of the UV lamp module 104 as well as providing a communications interface to a central controller monitoring a number of sanitization sensors 100 within a facility. As mentioned above, a sensor control chip 174 may be mounted on the main circuit board 180 to receive sensor data from the sensors 106-1, 106-2 on the sensor circuit board 170. The control circuit of the main circuit board 180 receives data from the sensor control chip 174 to optimize the UV light output from the UV lamp module 104 based on the operating conditions of the UV lamp module 104 and the sensed environmental conditions surrounding the sanitization system 100. Sensor data from the sensor circuit board 170 may be transferred to the main circuit board via an electrical connector 172. In embodiments, the electrical connector 172 may be a shielded, twisted pair wire connector to protect the data signal from sensors 106-1, 106-2 and to shield the data signals from interference from the UV lamp module 104.

The inverter circuit board 112 may be mounted to and spaced from the main circuit board 180 by two or more posts 184. The posts 184 are provided with a length which prevents electrical cross-talk between circuit boards 112 and 180. In one example, the posts 184 may be 1 inch long, but they may be longer or shorter in further embodiments. It is understood that the location of components and the functionality described above for the inverter board 112 and the main circuit board 180 may be shared differently between the two circuit boards 112 and 180 in further embodiments.

The fixture 110 including the pogo pins 124, 126 and the ramp 134 provide a novel and advantageous system for installing a UV lamp module. The size of the fixture slot and configuration of the ramp ensure that the UV lamp module may be quickly, easily, reliably and repeatably inserted for operation into the fixture. This eliminates the need for lengthy and cumbersome operations that conventionally required partial or total device disassembly. The UV lamp module 104 may just as quickly and easily be removed from the slot. A user may grip sides of the UV lamp module and pull it out of the slot. As noted above, the spring force of the pogo pins 124, 126 are controlled so that pulling on the module 104 will easily remove the slide plate 152 from the ramp recess 134-2, thus allowing easy removal of a module 104 for replacement.

In operation, a user need only unscrew or otherwise detach the slot cover plate 116 (FIG. 2), detach the pin connector 148 (FIG. 18) and then remove the existing UV lamp module 104 by manually gripping and pulling on the edges of the module 104. A new lamp module may be manually inserted until engagement of the lamp electrodes 154, 156 with pogo pins 124, 126, the pin connector 148 reattached, and the slot cover plated closed to complete the lamp replacement process.

In summary, embodiments of the present technology relate to a fixture configured to removably receive a UV lamp module comprising a slide plate and first and second electrodes, the fixture comprising: a base plate; a ramp formed on the base plate, the ramp comprising a first section at a first elevation from the base plate and a recess at a second elevation from the base plate, the second elevation smaller than the first elevation; and a pair of pogo pins positioned adjacent the ramp, the pogo pins configured to provide a voltage to the UV lamp module; wherein the fixture is configured to receive the UV lamp module by the slide plate sliding along the ramp until the slide plate seats within the recess; and wherein the first and second electrodes are aligned with and biased against the first and second pogo pins upon seating of the slide plate in the recess.

In a further aspect, the present technology relates to a fixture configured to removably receive a UV lamp module comprising a slide plate and first and second electrodes, the fixture comprising: a base plate; a ramp formed on the base plate, the ramp comprising a longitudinal axis, a first surface parallel to the base plate and spaced at a first elevation from the base plate and a recess parallel to the base plate and spaced at a second elevation from the base plate, the second elevation smaller than the first elevation; and a pair of pogo pins aligned with each other along an axis parallel to the longitudinal axis of the ramp, the pogo pins configured to provide a voltage to the UV lamp module; wherein the fixture is configured to receive the UV lamp module by the slide plate sliding along the ramp in a direction of the longitudinal axis until the slide plate seats within the recess; wherein the first and second electrodes are aligned with and biased against the first and second pogo pins upon seating of the slide plate in the recess; and wherein a first pogo pin of the pair of pogo pins configured to allow the first pogo pin to engage but slide past the first electrode enroute to engagement of the first pogo pin with the second electrode as the slide plate slides along the ramp.

In another aspect, the present technology relates to a method of affixing and powering a UV lamp module within a fixture, the UV lamp module comprising a slide plate and first and second electrodes, the method comprising: (a) manually inserting the UV lamp module into the fixture so that the slide plate slides along a ramp in the fixture; (b) sliding the first electrode into engagement and then past a first pogo pin within the fixture as the slide plate slides along the ramp; (c) seating the slide plate within a recess within the ramp when the slide plate reaches a point along the ramp; (d) engaging the first electrode with a second pogo pin within the fixture, and engaging the second electrode with the first pogo pin, upon seating of the slide plate within the recess, engagement of the first and second electrodes with the first and second pogo pins powering the UV lamp module.

It is understood that the present subject matter may be embodied in many different forms and should not be construed as being limited to the embodiments set forth herein. Rather, these embodiments are provided so that this subject matter will be thorough and complete and will fully convey the disclosure to those skilled in the art. Indeed, the subject matter is intended to cover alternatives, modifications and equivalents of these embodiments, which are included within the scope and spirit of the subject matter as defined by the appended claims. Furthermore, in the following detailed description of the present subject matter, numerous specific details are set forth in order to provide a thorough understanding of the present subject matter. However, it will be clear to those of ordinary skill in the art that the present subject matter may be practiced without such specific details.

The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The aspects of the disclosure herein were chosen and described in order to best explain the principles of the disclosure and the practical application, and to enable others of ordinary skill in the art to understand the disclosure with various modifications as are suited to the particular use contemplated.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A fixture configured to removably receive a UV lamp module comprising a slide plate and first and second electrodes, the fixture comprising:
   a base plate;
   a ramp formed on the base plate, the ramp comprising a first section at a first elevation from the base plate and a recess at a second elevation from the base plate, the second elevation smaller than the first elevation; and
   a pair of pogo pins positioned adjacent the ramp, the pogo pins configured to provide a voltage to the UV lamp module;
   wherein the fixture is configured to receive the UV lamp module by the slide plate sliding along the ramp until the slide plate seats within the recess; and
   wherein the first and second electrodes are aligned with and biased against the first and second pogo pins upon seating of the slide plate in the recess.

2. The fixture of claim 1, wherein first and second pogo pins of the pair of pogo pins are formed of brass with a gold plating for electrical conductivity.

3. The fixture of claim 1, wherein first and second pogo pins of the pair of pogo pins each comprise:
   a base section,
   a plunger, and
   a spring, the plunger configured to depress within the base section against a biasing force of the spring.

4. The fixture of claim 3, wherein the plunger of the first pogo pin is configured to depress within base section of the first pogo pin an amount allowing the first pogo pin to engage but slide past the first electrode enroute to engagement of the first pogo pin with the second electrode as the slide plate slides along the ramp.

5. The fixture of claim 1, wherein first and second pogo pins of the pair of pogo pins each comprise a radiused distal tip configured to allow the first pogo pin to engage but slide past the first electrode enroute to engagement of the first pogo pin with the second electrode as the slide plate slides along the ramp.

6. The fixture of claim 1, wherein first and second pogo pins of the pair of pogo pins provide haptic feedback upon engaging the first and second electrodes, the haptic feedback indicating full insertion of the UV lamp module into the fixture.

7. The fixture of claim 1, wherein seating of the slide plate within the recess provides haptic feedback, the haptic feedback indicating full insertion of the UV lamp module into the fixture.

8. The fixture of claim 1, further comprising a plurality of metal plates surrounding portions of the fixture, the plurality of metal plates forming a Faraday cage to shield an environment surrounding the fixture from electromagnetic radiation from the UV lamp module.

9. The fixture of claim 8, wherein the plurality of metal plates comprise a first plate in or on the base plate and a second plurality of plates extending perpendicularly from the base plate.

10. The fixture of claim 1, further comprising a sensor circuit board, the sensor circuit board comprising one or more sensors for sensing characteristics of an environment around the fixture, the sensed characteristics used to control operation of the UV lamp module.

11. A fixture configured to removably receive a UV lamp module comprising a slide plate and first and second electrodes, the fixture comprising:
    a base plate;
    a ramp formed on the base plate, the ramp comprising a longitudinal axis, a first surface parallel to the base plate and spaced at a first elevation from the base plate and a recess parallel to the base plate and spaced at a second elevation from the base plate, the second elevation smaller than the first elevation; and
    a pair of pogo pins aligned with each other along an axis parallel to the longitudinal axis of the ramp, the pogo pins configured to provide a voltage to the UV lamp module;
    wherein the fixture is configured to receive the UV lamp module by the slide plate sliding along the ramp in a direction of the longitudinal axis until the slide plate seats within the recess;
    wherein the first and second electrodes are aligned with and biased against the first and second pogo pins upon seating of the slide plate in the recess; and
    wherein a first pogo pin of the pair of pogo pins configured to allow the first pogo pin to engage but slide past the first electrode enroute to engagement of the first pogo pin with the second electrode as the slide plate slides along the ramp.

12. The fixture of claim 11, wherein first and second pogo pins of the pair of pogo pins are formed of brass with a gold plating for electrical conductivity.

13. The fixture of claim 11, wherein first and second pogo pins of the pair of pogo pins each comprise:
   a base section,
   a plunger, and
   a spring, the plunger configured to depress within the base section against a biasing force of the spring,
   wherein the plunger of the first pogo pin is configured to depress within base section of the first pogo pin an amount allowing the first pogo pin to engage but slide past the first electrode enroute to engagement of the first pogo pin with the second electrode as the slide plate slides along the ramp.

14. The fixture of claim 11, wherein first and second pogo pins of the pair of pogo pins each comprise a radiused distal tip configured to allow the first pogo pin to engage but slide past the first electrode enroute to engagement of the first pogo pin with the second electrode as the slide plate slides along the ramp.

15. The socket of claim 11, further comprising a plurality of metal plates surrounding portions of the fixture, the plurality of metal plates forming a Faraday cage to shield an environment surrounding the fixture from electromagnetic radiation from the UV lamp module.

16. The fixture of claim 11, further comprising a sensor circuit board, the sensor circuit board comprising one or more sensors for sensing characteristics of an environment around the fixture, the sensed characteristics used to control operation of the UV lamp module.

17. A method of affixing and powering a UV lamp module within a fixture, the UV lamp module comprising a slide plate and first and second electrodes, the method comprising:
   (a) manually inserting the UV lamp module into the fixture so that the slide plate slides along a ramp in the fixture;
   (b) sliding the first electrode into engagement and then past a first pogo pin within the fixture as the slide plate slides along the ramp;
   (c) seating the slide plate within a recess within the ramp when the slide plate reaches a point along the ramp; and
   (d) engaging the first electrode with a second pogo pin within the fixture, and engaging the second electrode with the first pogo pin, upon seating of the slide plate within the recess, engagement of the first and second electrodes with the first and second pogo pins powering the UV lamp module.

18. The method of claim 17, further comprising the step of providing haptic feedback upon seating of the slide plate within the recess and engaging the first and second electrodes with the first and second pogo pins, the haptic feedback indicating full insertion of the UV lamp module into the fixture.

19. The method of claim 17, further comprising the step of electrically coupling a pin connector to a circuit board on the UV lamp module to allow signal communication between an electronic component within the fixture and the UV lamp module.

20. The method of claim 17, further comprising the step of removing the UV lamp module from the fixture by gripping edges of the UV lamp module and pulling the lamp module out of the fixture.

* * * * *